(12) United States Patent
Eberhard (10) Patent No.: US 8,596,266 B2
(45) Date of Patent: Dec. 3, 2013

(54) DISCHARGING DEVICE

(75) Inventor: Thomas Eberhard, Radolfzell (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 318 days.

(21) Appl. No.: 12/924,786

(22) Filed: Oct. 4, 2010

(65) Prior Publication Data

US 2011/0083666 A1    Apr. 14, 2011

(30) Foreign Application Priority Data

Oct. 13, 2009 (DE) .......................... 10 2009 049 902

(51) Int. Cl.
*A61M 15/00*   (2006.01)

(52) U.S. Cl.
USPC ............ 128/200.23; 128/200.14; 128/200.24; 222/153.01; 222/321.8; 222/321.9

(58) Field of Classification Search
None
See application file for complete search history.

(56) References Cited

U.S. PATENT DOCUMENTS

| | | | |
|---|---|---|---|
| 5,226,563 A | 7/1993 | Coggiola | |
| 5,427,280 A * | 6/1995 | Fuchs | ............................ 222/320 |
| 6,305,580 B1 * | 10/2001 | Chen | ............................ 222/162 |
| 6,446,839 B1 | 9/2002 | Ritsche | |
| 7,302,948 B2 | 12/2007 | Anderson | |
| 2001/0007327 A1 * | 7/2001 | Ritsche et al. | .................. 222/82 |
| 2005/0098172 A1 | 5/2005 | Anderson | |
| 2006/0016833 A1 * | 1/2006 | Greiner-Perth | ............. 222/383.1 |
| 2006/0255072 A1 | 11/2006 | Hagin et al. | |
| 2007/0131717 A1 * | 6/2007 | Davies et al. | .................. 222/162 |
| 2008/0210228 A1 * | 9/2008 | Corbacho | ................ 128/200.22 |

FOREIGN PATENT DOCUMENTS

| | | |
|---|---|---|
| DE | 692 00 604 T2 | 5/1995 |
| DE | 199 40 234 A1 | 3/2001 |
| EP | 0 509 863 A1 | 10/1992 |
| FR | 2 682 305 | 4/1993 |
| WO | WO 03/074189 A1 | 9/2003 |

OTHER PUBLICATIONS

Office Action of German Patent Office dated Jun. 18, 2010 (5 pages).
European Patent Office Search Report dated Feb. 8, 2011 (8 pages) with English translation of categories of cited documents.

* cited by examiner

*Primary Examiner* — Jackie Ho
*Assistant Examiner* — Eric Bryant
(74) *Attorney, Agent, or Firm* — Flynn, Thiel, Boutell & Tanis, P.C.

(57) ABSTRACT

A discharging device, particularly for a pharmaceutical liquid, is adapted to accommodate and actuate a pump-type dispenser in an accommodating region.
In the delivered state, the accommodating region of the discharging device is sufficiently large to ensure that the pump-type dispenser can be accommodated by the accommodating region when the dispenser has not yet been actuated and does not yet communicate with the outlet passageway. The discharging device is particularly useful for pharmaceutical liquids prone to oxidation and thus in need of extensive protection from contact with air.

15 Claims, 4 Drawing Sheets

DISCHARGING DEVICE

TECHNICAL FIELD AND PRIOR ART

The invention relates to a discharging device for a liquid, more particularly a pharmaceutical liquid, which discharging device is capable of accommodating and actuating a pump-type dispenser. This application claims the priority of the German patent application No. 10 2009 049 902.4. The whole disclosure of this prior application is herewith incorporated by reference into this application.

A generic discharging device has a pump-type dispenser, which in turn has a liquid receptacle, a pumping mechanism, and an outlet port comprising an outlet passageway, said pumping mechanism being actuatable by depressing the outlet port in the direction of the liquid receptacle. Another generic discharging device further comprises an accommodating region for the at least partial accommodation of the pump-type dispenser comprising an outlet port receiver and a liquid passageway, wherein the outlet port receiver and the outlet port are designed to interengage such that the liquid passageway provides liquid-conducting, leak-proof communication in a relative end position, and a force transferring surface disposed such that the displacement of said force transferring surface in the direction of the outlet port receiver causes the liquid receptacle of the pump-type dispenser to be likewise displaced in the direction of the outlet port receiver. A generic discharging device is also equipped with two housing portions displaceably guided by means of a guiding mechanism in relation to each other, the outlet port being immovably disposed on one of these housing portions and the force transferring surface being immovably disposed on the other housing portion.

A generic discharging device is designed to accommodate a standard pump-type dispenser, which in turn already comprises the essential components for storing and conveying a pharmaceutical liquid. The parts of the discharging device enclosing the pump-type dispenser, such as the two housing portions, serve to facilitate the manipulation of said pump-type dispenser, to direct the liquid conveyed by the pump-type dispenser to a discharge orifice, to cause vortexing of the liquid in the vicinity of said discharge orifice, and optionally to provide a additional functionality, such as counting of the discharge shots already performed, by means of an electronic counting module.

For the purpose of actuating the pump-type dispenser, two housing portions are provided, of which, in generic discharging devices, one housing portion usually forms a main portion, in relation to which the other housing portion is displaceable as an actuating portion guided by the guiding mechanism. Depending on the intended use, the accommodating region is diminished by the displacement of the housing portions. In other words, the force transferring surfaces and the outlet port receiver, which are arranged on opposite sides of the accommodating region, are caused to approach each other in order to actuate the pumping mechanism of the pump-type dispenser. Preferably, the aforementioned discharge orifice for discharging the liquid is present on the housing portion that has the outlet port receiver.

In generic discharging devices, the outlet port of the pump-type dispenser and the outlet port receiver are, in the delivered state, generally already pushed together and thus non-positively interengaged. The outlet port receiver and the outlet port are thus already coupled to each other during assembly due to insertion of the outlet port into the outlet port receiver. If the force for this is exerted on the liquid receptacle of the pump-type dispenser, however, this is accompanied by an initial actuation of the pump-type dispenser because of the resultant displacement of the outlet port in relation to the liquid receptacle of the pump-type dispenser. This is regarded as being an advantage because it results in air being sucked into the pump-type dispenser during the assembly of the discharging device in order to equalize the volume, which in turn can lead to a contamination or oxidation effect. An inert gas atmosphere optionally introduced into the pump-type dispenser during the manufacture thereof may be diluted or expelled by this initial actuation during assembly.

Object and its Achievement

It is an object of the invention to improve a generic discharging device such that the latter is able to remain in a neutral state until initially actuated by the patient, and in particular, that an inert gas atmosphere is not diluted during assembly.

Another object of the invention is to provide a suitable method for the assembling and priming a discharging device.

According to the invention, this object is achieved in that the two housing portions and thus the outlet port receiver and the force transferring surface are spaced apart from each other in a delivered state of the discharging device such that the outlet port is located in a relative position, in relation to the outlet port receiver, that is at a distance from the relative end position, and in that the housing portions are displaceable relatively to each other in such a way that the displacement of said housing portions is capable of bringing the outlet port into its relative end position, in relation to the outlet port receiver.

According to the invention, the accommodating region, i.e., the region between the outlet port receiver and the force transferring surface, has, in the delivered state, a size which allows for the accommodation of the pump-type dispenser therein in the neutral state, without having to position the outlet port in its relative end position, in relation to the outlet port receiver. The pump-type dispenser can be completely or partially disposed in the accommodating region. However, it is essential for the force transferring surface to be prepositioned, in this delivered state, in relation to that part of the liquid receptacle on which a force can be exerted for the purpose of causing displacement of the force transferring surface in the direction of the outlet port receiver, leading to touch contact of the force transferring surface with this part of the liquid receptacle, so that the displacement of the force transferring surface causes the outlet port of the pump-type dispenser to be pressed into the outlet port receiver. The delivered state is therefore that state in which the discharging device is delivered to the end customer, i.e., the patient, usually along with an outer package such as a folding box and a package insert with instructions for the medication.

The necessary force for bringing the outlet port into this relative end position is not applied during assembly of the discharging device, but is instead initially applied by the patient, preferably during the course of priming the discharging device, involving displacement of the force transferring surface relatively to the outlet port receiver. If this is brought about by displacement of the housing portions in relation to each other, which are to be displaced relatively to each other in order to bring about a discharge when the device is used in accordance with the intended purpose, the procedure for priming by the patient is essentially the same as with standard discharging devices. The same method of actuation hitherto used with generic discharging devices for discharging the liquid is likewise used with discharging devices of the invention during the course of priming, both for bringing the outlet port into its final position relative to the outlet port receiver and for priming the pump-type dispenser.

The housing portions are guided in relation to each other by a guiding mechanism. Preferably, is given to this guiding mechanism is designed to guide translatively along a main direction of extension of the discharging device that coincides with the direction of actuation of the pump-type dispenser.

For easier displacement of the housing portions in relation to each other, each of these preferably has finger rest surfaces, while it is particularly preferred for the housing portion comprising the discharge orifice to have two finger rests one on each side of the discharge orifice for the index finger and the middle finger and for the housing portion comprising the force transferring surface to have a thumb rest. However, it is not compulsory for both housing portions to be directly accessible to the patient for transferring force. Also covered are embodiments of the invention in which at least one of the housing portions is only indirectly displaceable, say, by means of a manual actuator affixed to the main housing portion, which, when actuated indirectly, causes displacement of the housing portion that is in this case configured as an internal housing portion disposed inside the main housing portion. The direction of actuation of such a separate manual actuator may thus differ from the direction of displacement of the housing portion.

In order to achieve and maintain a reliable liquid-conducting and leak-proof connection between the outlet port receiver and the outlet port in their relative end position, the outlet port and the outlet port receiver are preferably non-positively held against each other in the relative end position, the force required for separation thereof being greater than the force exerted by the weight of the pump-type dispenser. Thus the engagement of the outlet port with the outlet port receiver achieved during the course of the priming is maintained throughout the useful life of the discharging device, or at least of the pump-type dispenser, subsequently to the priming operation. It is regarded as being particularly advantageous when the outlet port and the outlet port receiver have matching cylindrical portions, the outside diameter of the cylindrical portion of the outlet port and the inside diameter of the cylindrical portion of the outlet port receiver being designed to give a non-positive press fit in the relative end position with these cylindrical portions preferably not engaging with each other in the delivered state. However, configurations in which the inside diameter of the outlet port and the outside diameter of the outlet port receiver are designed to achieve such a press fit are also conceivable. The force for achieving the press fit must be applied by the patient and is therefore preferably less than 50 newtons.

In order to achieve reliable interengagement of the cylindrical portions with each other, an insertion slope may be provided on one of the cylindrical portions or on both cylindrical portions.

The relative end position is the position of the outlet port relative to the outlet port receiver that is provided in normal use. For defining the relative end position, it is preferred to provide the outlet port receiver with a stop member against which the outlet port abuts during the course of interengagement. This stop member ensures that the displacement of the force transferring surface relatively to the outlet port receiver brings about a specific pump stroke, since the relative end position of the outlet port and the outlet port receiver is particularly clearly defined.

Particularly advantageous is the use of a discharging device of the invention in conjunction with an inert gas atmosphere present in the pump-type dispenser in the delivered state, in particular a protective nitrogen atmosphere or a protective carbon dioxide atmosphere. This inert gas atmosphere, which can in particular have an antioxidant or decontaminant action, is introduced into the pump-type dispenser during filling thereof. Owing to the configuration of the device according to the invention, the inert gas atmosphere is not diluted until the patient primes the discharging device when actuating it for the first time. Also advantageous is the use of the discharging device of the invention with a pump-type dispenser in which the pumping mechanism is connected to the liquid receptacle via a connecting passageway and wherein, in the delivered state, the liquid is only present in the liquid receptacle itself and in the connecting passageway. With such a configuration in which the liquid is, in the delivered state, primarily present in the liquid receptacle and, in particular, has not yet reached the pumping mechanism, there is no danger of an adverse effect arising due to the interaction of the liquid with parts of the pumping mechanism, for example metal parts. The pumping mechanism does not come into contact with the liquid until the patient primes the discharging device when actuating it for the first time.

Preference is given to a configuration of the housing portions such that the maximum spacing between the force transferring surface and the outlet port receiver after the initial actuation is smaller than the spacing between the force transferring surface and the outlet port receiver in the delivered state. Thus, after the priming has been performed by actuating the discharging device for the first time, the accommodating region for the pump-type dispenser will not assume the same size as it previously had in the delivered state. This ensures that the outlet port of the pump-type dispenser cannot become detached from the outlet port receiver after priming. Preferably, these situations are achieved by locking means which prevent the force transferring surface from returning to its position relative to the outlet port receiver in the delivered state after priming has taken place.

Such locking means, for example, can be present in the vicinity of the guiding mechanism of the housing portions. In such a case the guiding mechanism is designed such that it only allows limited relative mobility of the housing portions in relation to each other after the priming has taken place.

Alternatively, it is possible for a first housing portion of the two housing portions to consist of two parts, of which a initial housing sub-portion of the first housing portion has the force transferring surface or the outlet port receiver and a second housing sub-portion of the first housing portion comprises, together with the second housing portion, the guiding mechanism for ensuring guided movement of the housing portions relatively to each other. The two housing sub-portions are thus attached to each other such that they are displaceable relatively to each other. With this design, special provision for the guiding mechanism between the housing portions to restrict their freedom of movement after priming is not necessary. Thus the guiding mechanism can be non-variably configured to permit only such relative displacement of the housing portions as is substantially equal to the pump stroke of the pumping mechanism of the pump-type dispenser. The additional displacement distance that is required to keep the outlet port at a distance from the relative end position, in relation to the outlet port receiver, in the delivered state is achieved by the two-part design of the first housing portion. In the delivered state, the two housing sub-portions of the first housing portion are thus in a first relative position, which during the course of the priming is shifted to a second relative position. The relative displacement preferably takes place in the same direction as that in which the guiding mechanism guides the two housing portions relatively to each other.

Preferably, matching stop devices are provided on the second housing sub-portion of the first housing portion and on the second housing portion so as to prevent detachment of the second sub-portion from the second housing portion in a form-fitting manner. These stop devices are configured and/or aligned such that they allow relative displacement of the second housing sub-portion in relation to the second housing portion that is substantially equal to the pump stroke of the pumping mechanism of the pump-type dispenser.

Particular preference is given to a configuration in which at least one locking means is present on the second housing sub-portion, which locking means extends into a recess in a wall of the second housing portion or extends through this recess and prevents displacement of the second housing sub-portion as long as there is a cap on the second housing sub-portion. Particularly as regards the presence of such a locking means, it is advantageous when the first housing portion consists of two parts, since in such a case the second housing sub-portion can be prepositioned, in the delivered state, such that the locking portion extends into, or is positioned directly in front of, the recess in a wall of the second housing portion. The purpose of the locking means is to prevent inadvertent actuation of the discharging device due to displacement of the second housing portion relatively to the first housing portion, which would result in a discharge, this only being possible when the cap is removed.

In the configuration involving two housing sub-portions, it is regarded as being particularly preferable for the housing sub-portions to have matching locking means, by means of which the housing sub-portions can be attached to each other in two different relative positions. Thus a first relative position of the housing sub-portions corresponds to the delivered state and a second relative position corresponds to the operating state achieved following the initial actuation and maintained thereafter. Preferably, the relative position of the initial housing sub-portion in relation to the second housing sub-portion differs between the two relative positions approximately by the distance at which the outlet port is spaced from its relative end position, in relation to the outlet port receiver, in the delivered state.

The invention further relates to a method for assembling and priming a discharging device of the type described above, in which, in an assembly step, the housing portions are pushed into each other such that the force transferring surface remains sufficiently far from the outlet port receiver that the outlet port is still not disposed in a relative end position in relation to the outlet port receiver when the pump-type dispenser rests against the force transferring surface, and in which, in an initial actuating step following the assembly step after delivery to the patient, the outlet port is moved to its relative end position in relation to the outlet port [receiver] caused by the patient pushing the housing portions further into each other.

BRIEF DESCRIPTION OF THE DRAWINGS

Other aspects and advantages of the invention are revealed by the claims and by the following description of a preferred exemplary embodiment of the invention, which is explained below with reference to the figures, in which:

DETAILED DESCRIPTION OF THE EXEMPLARY EMBODIMENT

Figure 1:
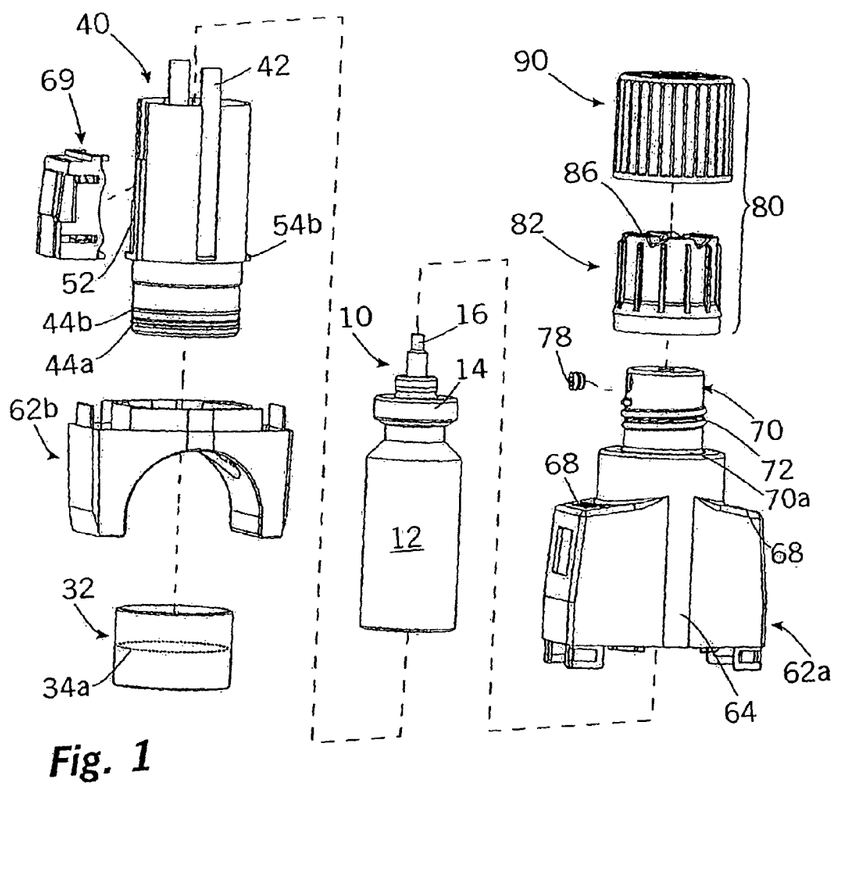
FIG. 1 is an exploded view of a discharging device of the invention.
Figure 2A:
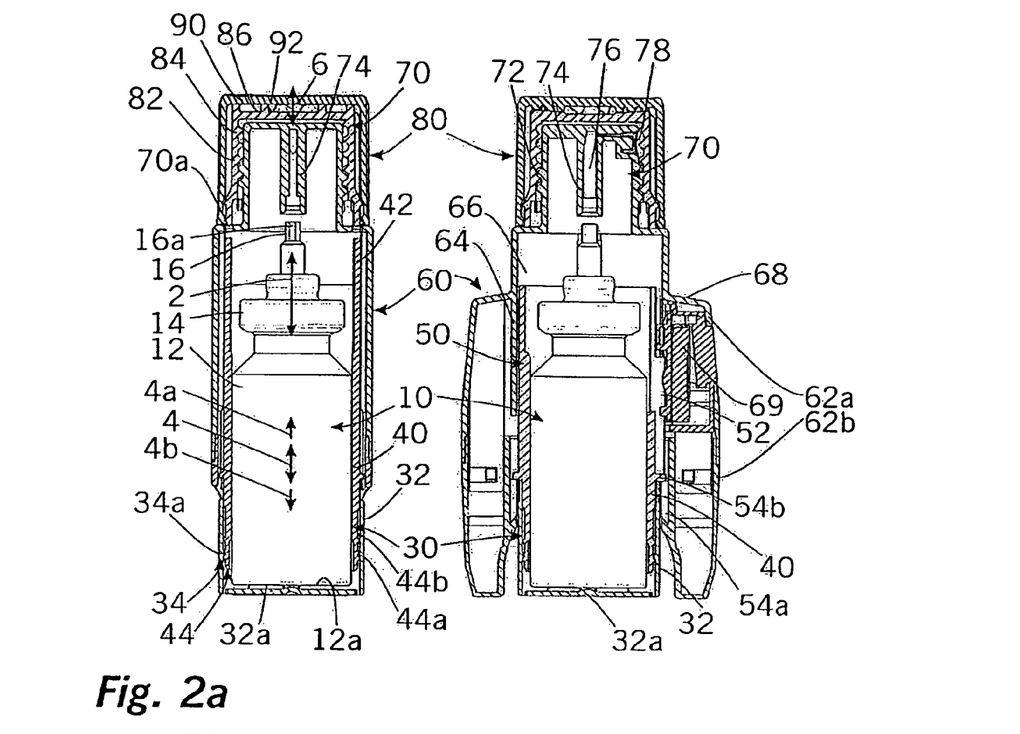
FIGS. 2a to 2e show the discharging device shown in FIG. 1 in various stages, including the delivered state, the initial actuation, and the interengaged state.

With reference to FIGS. 1 and 2a, the design of the exemplary embodiment illustrated is described below.

The discharging device of the invention comprises a pump-type dispenser 10 and two housing portions 30, 60, and a cap 80.

The pump-type dispenser 10 is a standard pump-type dispenser having a liquid receptacle 12, a pumping mechanism 14, not shown in any greater detail, and an outlet port 16. The outlet port 16 is displaceable relatively to the liquid receptacle 12 in the pumping direction 2 in order to actuate the pumping mechanism 14 and cause a discharge of liquid from the liquid receptacle 12 through an outlet passageway 16a of the outlet port 16.

In use, the two housing portions 30, 60 are designed to be displaceable relatively to each other in the direction of the arrow 4 with the aid of a guiding mechanism 50 to be explained below.

The housing portion 60 forms a main portion 60 of the illustrated discharging device. It consists of two parts 62a and 62b, which are attached to each other during assembly and remain in a fixed relationship to each other, for which reason they are jointly referred to below as the main portion 60. Said main portion 60 has an approximately cylindrical internal portion 64 enclosing an accommodating chamber 66. Two finger rests 68 project outwardly from each side away from this internal portion 64, and an accommodating region for an electronic counting module 69 is provided under one of the two finger rests. The main portion 60 is bottom open in order to ensure good handling of the pump-type dispenser 10 accommodated therein and of the first housing portion 30. On its opposite top side, the main portion 60 has a spray head 70, on the outside of which a male thread 72 is formed. An outlet port receiver 74 for accommodating the outlet port 16 of the pump-type dispenser 10 is present inside the spray head 70. A liquid passageway 76 affording communication between the outlet port receiver 74 and a discharge orifice 78 is present in said outlet port receiver 74.

The other housing portion 30 includes an actuation portion 30, which in turn has a first housing sub-portion 32 and a second housing sub-portion 40. The second housing sub-portion 40 is approximately tubular and, in terms of its inside diameter, suitable for accommodating the pump-type dispenser 10. On this tubular element 40 there are formed extensions 42, the ends of which are, in the delivered state, situated directly in front of corresponding apertures 70a in the main portion 60. On the side of the tubular element 40 facing away from the outlet port receiver 74, the initial housing sub-portion 32 of the actuation portion 30 is provided, which is configured as a cup-shaped base element 32. This base element 32 is pushed onto the end of the tubular element 40.

The cap 80 consists of two parts and has an internal part 82 with a female thread 84. On this internal part 82, which is inaccessible to the patient with the cap in place, is positioned an external part 90, which is displaceable in the direction of the arrow 6 relatively to the internal part 82, and an end face 86 of the internal part 82 and the inside surface 92 of the external part 90 are designed to interengage in a form-fitting and non-rotatable manner when the external part 90 is pressed against the internal part 82.

As mentioned above, a guiding mechanism 50 is provided that allows and restricts relative movement of the tubular element 40 in relation to the internal portion 64 of the main portion 60. This guiding mechanism 50 is mainly formed by adapting the outside diameter of the tubular element 40 to match the inside diameter of the internal portion 64, which gives rise to the relative mobility in the direction of the arrow 4. Furthermore, a radially outwardly projecting extension 52 on the tubular element 40 ensures that rotational mobility about an axis of the tubular element 40 defined by the arrow 4 in relation to the internal portion 64 is not possible. In addition stops members 54a and 54b are assigned to the guiding means. The stop 54b is present on the tubular element 40 as a radially outwardly projecting extension. Jointly with the stop 54a present on the part 62a, the stop 54b restricts the mobility of the tubular element 40 in the direction of the arrow.

As explained above, the base element 32 is also displaceable relatively to the tubular element 40. Locking means 34, 44 are provided which cooperate with each other on the tubular element 40 as well as on the base element 32. The locking means 34, 44 consist of an inwardly facing locking ring 34a on the base element 32 and two grooves 44a and 44b outwardly open on the tubular element 40. Thus, depending on the position of the grooves 44a and 44b in which the locking ring 34a engages, the base element 32 can be locked in two different relative positions on the tubular element 40.

The way in which the device is operated by the patient is explained below with reference to FIGS. 2a - 2e.

FIG. 2a shows the delivered state of the discharging device. In this delivered state the cap 80 is screwed right down onto the main portion 60 of the discharging device. The tubular element 40 is positioned within the internal portion 64 of the main portion 60 and is in its bottom end position so that the stop member 54b rests on the stop member 54a. The bottom portion 32 of the actuation portion 30 is in its lower initial relative position in relation to the tubular element 40, which is characterized by the engagement of the locking ring 34a in the bottom locking groove 44a. The pump-type dispenser 10 is in the neutral state. A bottom closure surface 12a of the liquid receptacle 12 lies on a force transferring surface 32a of the cup-shaped element 32. Due to the alignment of the base element 32 relative to the tubular element 40 and due to the alignment of the tubular element 40 relative to the internal portion 64 of the main portion 60, this force transferring surface 32a is sufficiently spaced apart from the outlet port receiver 74 for the outlet port 16 of the pump-type dispenser 10 to not yet be in force-fitting engagement with the outlet port receiver 74.

In a manner not illustrated, there is at this time an inert gas atmosphere still present in the pump-type dispenser 10, which inert gas atmosphere had been introduced during the manufacture of the pump-type dispenser 10 and has remained intact up to the time signified by FIG. 2a due to the fact that no initial displacement of the outlet port 16 relatively to the liquid receptacle 12 has as yet occurred.

Starting from the state shown in FIG. 2a, operation of the device is started by removing the cap 80. When this has been done, the initial actuation is performed by the patient placing their index finger and middle finger on the finger rests 68 and using their thumb to press the bottom portion 32 of the actuation portion 30 upwardly in the direction of the arrow 4a.

Doing so brings about two different relative displacements.

On the one hand the actuation portion 30 is in its entirety relatively displaced by the distance $I_1$ in relation to the internal portion 64. This relative displacement is possible because by removing the cap 80, the extensions 42 on the tubular element 40 are able to slide through the recesses 70a into the region previously occupied by the cap 80. On the other hand, the bottom portion 32 is relatively displaced by the distance $I_2$ in relation to the tubular element 40. Under the action of the actuation force, the locking ring 34a slides out of the initial locking groove 44a and into the second locking groove 44b of the tubular element 40.

Jointly with the bottom portion 32, the liquid receptacle 12 of the pump-type dispenser 10 is also raised relatively to the tubular element 40 in the direction of the arrow 4a by the distance $I_2$. The displacement of the tubular element 40 causes simultaneous displacement of the liquid receptacle 12 in relation to the internal portion 64 by the distance $I_1$. A displacement of the liquid receptacle 12 by the distance $I_1+I_2$ in relation to the internal portion 64 is thus brought about with the initial actuation carried out when priming the device.

The result of this displacement of the liquid receptacle 12 of the pump-type dispenser 10 by the distance $I_1+I_2$ is as follows: Firstly, the outlet port 16 approaches the insertion slope 74a of the outlet port receiver 74 but without being inserted into the same at this stage. Next, a displacement of the outlet port 16 in relation to the liquid receptacle 12 takes place, bringing about an initial pumping action of the pumping mechanism 14. Once the pumping mechanism has reached its actuated end position, the outlet port 16 is no longer displaceable relatively to the liquid receptacle 12 and is thus inserted into the outlet port receiver 74, wherein, owing to the adaptation of the diameter 16b of the outlet port 16 and the diameter 74a of the outlet port receiver 74 to each other, a non-positive press fit is established. This initial actuation does not result in a shot of liquid, as initially only air is expelled from the pump chamber of the pumping mechanism 14.

Figure 2B:
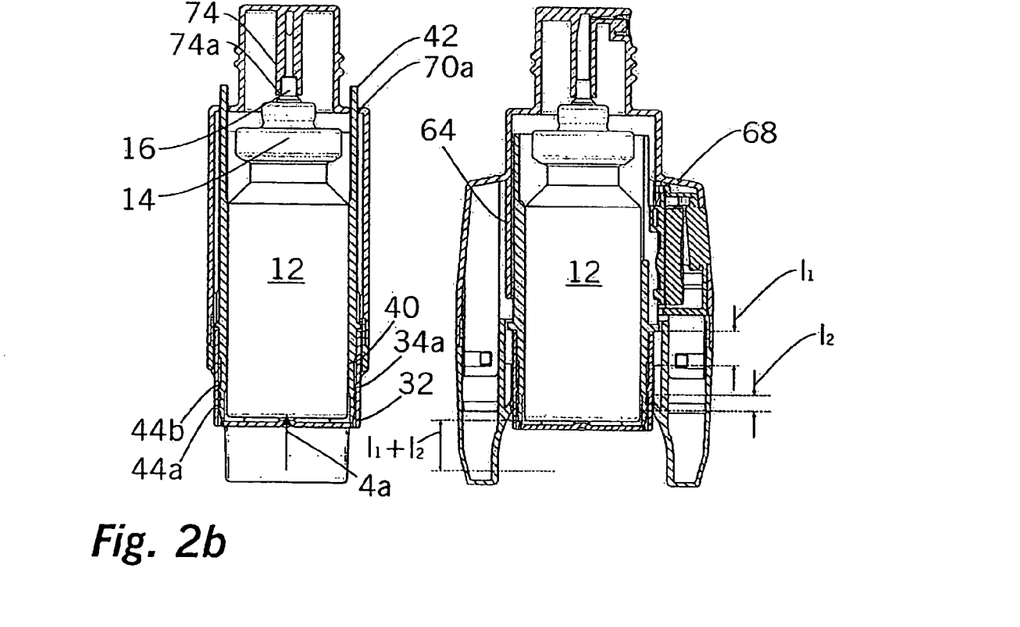

In this manner the compressed state shown in FIG. 2b is attained and priming of the discharging device is complete.

Figure 2C:
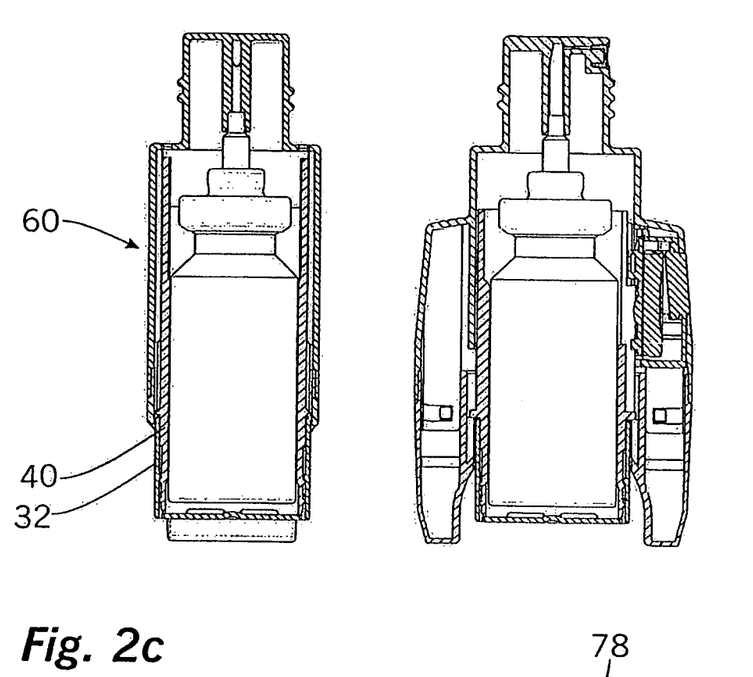
Figure 2D:
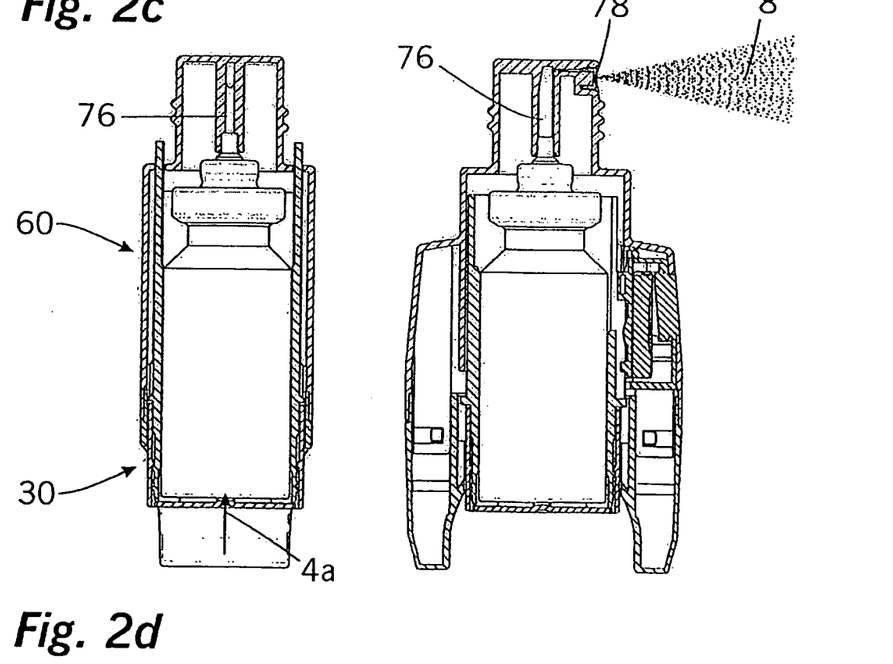

When the patient stops exerting force on the cup-shaped element 32 in the direction of the main portion 60, the pump-type dispenser 10 returns to its neutral state, thereby displacing the tubular element 40 back to its starting position shown in FIG. 2a in the manner illustrated in FIG. 2c, in other words, to a position in which the stops members 54a and 54b abut each another. A return displacement of the base element 32 in relation to the tubular element 40, however, does not take place, since the displacement of the tubular element 40 relative to the main portion 60 would be equal to a full pump stroke of the pumping mechanism 14.

A further actuation starting from the state shown in FIG. 2c and brought about by exerting force on the actuation portion 30, which is no longer movable in relation to the main portion 60, in turn causes a shot of liquid from the liquid receptacle 12 through the passageway 76 to the discharge orifice 78, from which the liquid is then emitted as a spray jet 8. When the actuation has taken place and force is no longer exerted on the actuation portion 30 in relation to the main portion 60 in the direction of the arrow 4a, the discharging device returns to the state shown in FIG. 2c.

Figure 2E:
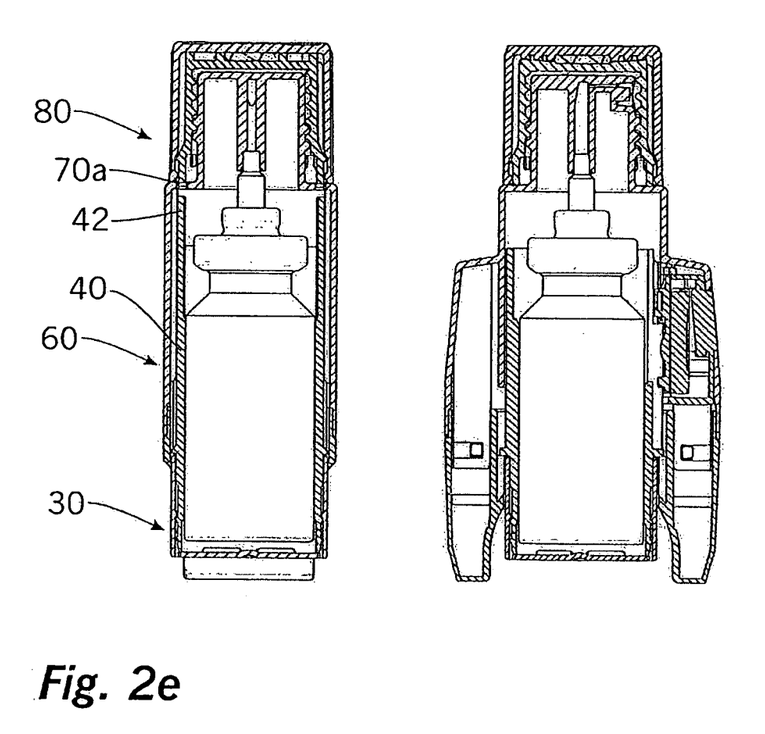

As FIG. 2e shows, once it has been operated, the discharging device can then be secured against inadvertent actuation and unwanted shots by replacing the cap 80. With the cap 80 in place, displacement of the actuation portion 30 in relation to the main portion 60 is no longer possible, since the locking extensions 42 formed on the tubular element 40 are not able to slide through the recesses 70a, these being blocked by the cap 80. The state shown in FIG. 2e thus prevents, say, a child from triggering a shot, assuming that the child is unable to remove the safety cap 80 from the discharging device.

The invention claimed is:
1. A discharging device for a liquid that is adapted to accommodate and actuate a pump-type dispenser comprising:

a pump-type dispenser having a liquid receptacle, a pumping mechanism, and an outlet port comprising an outlet passage, which pumping mechanism can be actuated by depressing the outlet port in the direction of the liquid receptacle, an accommodating region for the at least partial accommodation of the pump-type dispenser, comprising
an outlet port receiver comprising a liquid passageway, said outlet port receiver and said outlet port being in a relative end position for creating a liquid-guiding and leak-proof connection between said liquid passageway and said outlet passage, and a force-transferring surface, on which a bottom surface of the liquid receptacle is disposed such that the displacement of said force-transferring surface in the direction of said outlet port receiver causes the liquid receptacle of said pump-type dispenser to be displaced in the direction of said outlet port receiver, and two mutually displaceable housing portions guided by a guiding mechanism, said outlet port receiver being immovably mounted on one of said housing portions while said force-transferring surface is immovably provided on the other housing portion, wherein in a delivered state, said two housing portions and thereby said outlet port receiver and said force-transferring surface are spaced apart such that said outlet port is disposed in a position relative to said outlet port receiver which is at a distance from said relative end position, and said two housing portions are movable relatively to each other such that said outlet port is movable to an end position relative to said outlet port receiver by displacement of said housing portions, wherein a first housing portion of said two housing portions is in the form of a two-membered housing portion, wherein a first housing sub-portion of said first housing portion comprises the force-transferring surface and a second housing sub-portion of said first housing portion comprises, together with said second housing portion, said guiding mechanism for the purpose of effecting guided movement of said housing portions relatively to each other, and said two housing sub-portions are mounted for moving relatively to each other, the first housing sub-portion being lockable to the second housing sub-portion.

2. The discharging device as defined in claim 1, wherein said outlet port and said outlet port receiver have matching cylindrical portions, and an outside diameter of the cylindrical portion of said outlet port and an inside diameter of the cylindrical portion of said outlet port receiver are such as to yield a non-positive press fit connection in the relative end position and said cylindrical portions do not interengage in the delivered state.

3. The discharging device as defined in claim 1, wherein a stop member is provided on said outlet port receiver to define said relative end position.

4. The discharging device as defined in claim 1, wherein in the delivered state in said pump-type dispenser there is a blanket of protective gas, and said pumping mechanism communicates with said liquid receptacle of said pump-type dispenser via a connecting passageway, and in the delivered state the liquid is present only in said liquid receptacle and in said connecting passageway.

5. The discharging device as defined in claim 1, wherein said two housing portions are formed such that the maximum distance between said force-transferring surface and said outlet port receiver after an initial actuation is less than the distance between said force-transferring surface and said outlet port receiver in the delivered state.

6. The discharging device as defined in claim 1, wherein matching stop members are provided on said second housing sub-portion of said first housing portion and on said second housing portion, wherein said stop members positively prevent detachment of said second housing sub-portion from said second housing portion.

7. The discharging device as defined in claim 1, wherein on said second housing sub-portion there is provided at least one locking portion which protrudes into a recess in a wall of said second housing portion or passes through the recess, to prevent displacement of said second housing sub-portion as long as a cap is mounted on said second housing portion.

8. The discharging device as defined in claim 1, wherein said housing sub-portions have matching locking means, by means of which they can be locked together in two different relative positions.

9. A method for assembling and priming a discharging device adapted to accommodate and actuate a pump-type dispenser,
the pump-type dispenser comprising a liquid receptacle, a pumping mechanism, and an outlet port having an outlet passage, wherein actuation is carried out by depressing said outlet port in the direction of said liquid receptacle, and comprising the steps of:
at least partially disposing said pump-type dispenser in an accommodating region delimited by two housing portions adapted to move relatively to each other,
providing on one of said housing portions an outlet port receiver for the accommodation of said outlet port and providing on said other housing portion a force-transferring surface for the purpose of displacing said liquid receptacle in the direction of said outlet port receiver,
in an assembly step, forcing the housing portions into each other such that said force-transferring surface is disposed sufficiently far from the outlet port receiver so that when the pump-type dispenser is in contact with the force-transferring surface, the outlet port is still not disposed in a relative end position in relation to the outlet port receiver, and
in a priming step following delivery to the patient, forcing said housing portions further into each other causing said outlet port to be moved to its relative end position in relation to said outlet port receiver.

10. A discharging device for a liquid adapted to accommodate and actuate a pump-type dispenser having a liquid receptacle with a bottom closure surface, a pumping mechanism, and an outlet port comprising an outlet passage, wherein the pumping mechanism is operable by movement of the outlet port in the direction of the liquid receptacle, the discharging device comprising:
a main housing portion having an open bottom for receiving the pump-type dispenser and at a top supporting an outlet port receiver defining a liquid passageway for receiving the outlet port of the pump-type dispenser to form a liquid-guiding and leak-proof connection between the liquid passageway and the outlet passage of the pump-type dispenser;
a base element including a force-transferring surface, wherein said force-transferring surface is configured for a surface-to-surface relationship with a bottom closure surface of the pump-type dispenser, wherein displacement of said base element in the direction of said outlet port receiver moves the liquid receptacle of the pump-type dispenser in the direction of said outlet port receiver;

a tubular element for receiving said base element; and a guiding mechanism for enabling displacement of said tubular element relative to said main housing portion, wherein said base element is lockable relative to said tubular element in a first position defining a delivered state relative to said outlet port receiver so that said force-transferring surface is located a distance from said outlet port receiver resulting in the outlet port of the pump-type dispenser being spaced from said outlet port receiver, wherein upon displacement of said base element toward said outlet port receiver, said base element is lockable relative to said tubular element in a second position defining an operable state whereat said outlet port receiver receives the outlet port of the pump-type dispenser, and wherein in the operable state the applying of force to said base element moves said base element and the pump-type dispenser toward said outlet port receiver resulting in dispensing of liquid from said discharging device.

11. The discharging device of claim 10, wherein said base element including said force-transferring surface comprises a cup-shaped element.

12. The discharging device of claim 10, including a cap secured to said main housing portion of said discharging device, wherein securing said cap to said main housing portion of said discharging device in the operable state prevents a user from moving said base element toward said outlet port receiver to dispense liquid.

13. The discharging device of claim 10, wherein said outlet port receiver and the outlet port have matching cylindrical portions, wherein an outside diameter of a cylindrical portion of the outlet port and an inside diameter of a cylindrical portion of said outlet port receiver yield a non-positive press fit connection in the operable state and do not interengage in the delivered state.

14. The discharging device of claim 10, wherein matching stop members provided on said tubular element and said main housing portion prevent detachment of said tubular element from said main housing portion.

15. The discharging device of claim 10, wherein said base element includes a locking ring and said tubular element includes spaced first and second locking grooves wherein said base element is locked relative to said tubular element in said first groove in the delivered state and said base element is locked relative to said tubular element in said second groove in the operable state.

* * * * *

UNITED STATES PATENT AND TRADEMARK OFFICE
CERTIFICATE OF CORRECTION

PATENT NO. : 8,596,266 B2  
APPLICATION NO. : 12/924786  
DATED : December 3, 2013  
INVENTOR(S) : Thomas Eberhard

Page 1 of 1

It is certified that error appears in the above-identified patent and that said Letters Patent is hereby corrected as shown below:

On the title page, change the Assignee to the one shown below:

(73) Assignee: APTAR RADOLFZELL GMBH, Radolfzell (DE)

Signed and Sealed this
Sixteenth Day of September, 2014

Michelle K. Lee
*Deputy Director of the United States Patent and Trademark Office*